US007882837B2

(12) United States Patent
Kwok et al.

(10) Patent No.: US 7,882,837 B2
(45) Date of Patent: Feb. 8, 2011

(54) FOREHEAD SUPPORT FOR FACIAL MASK

(75) Inventors: Philip Rodney Kwok, Chatswood (AU); William Edwin John Grant, Rotherhithe (GB); Robert Stephen Matchett, Mosman (AU)

(73) Assignee: ResMed Limited, Bella Vista (AU)

( * ) Notice: Subject to any disclaimer, the term of this patent is extended or adjusted under 35 U.S.C. 154(b) by 1098 days.

(21) Appl. No.: 11/207,006

(22) Filed: Aug. 19, 2005

(65) Prior Publication Data
US 2006/0011202 A1    Jan. 19, 2006

Related U.S. Application Data

(60) Continuation of application No. 10/661,570, filed on Sep. 15, 2003, now Pat. No. 6,997,188, which is a continuation of application No. 10/230,169, filed on Aug. 29, 2002, now Pat. No. 6,691,708, which is a division of application No. 09/608,440, filed on Jun. 30, 2000, now Pat. No. 6,463,931, which is a continuation of application No. 09/008,708, filed on Jan. 16, 1998, now Pat. No. 6,119,693.

(51) Int. Cl.
*A61M 16/00* (2006.01)

(52) U.S. Cl. ............... 128/207.11; 128/207.18; 128/206.21; 128/206.24; 128/206.28; 128/112.1; 128/115.1; 128/857; 2/255; 5/652.1

(58) Field of Classification Search ............... 128/112.1, 128/115.1, 116.1, 117.1, 121.1, 125.1, 207.17, 128/206.21, 206.24, 207.12
See application file for complete search history.

(56) References Cited

U.S. PATENT DOCUMENTS

| 4,429 | A | * | 3/1846 | Cooke et al. ............. 128/108.1 |
| 781,516 | A | | 1/1905 | Guthrie |
| 812,706 | A | | 2/1906 | Warbasse |
| 1,081,745 | A | | 12/1913 | Johnston et al. |
| 1,192,186 | A | | 7/1916 | Greene |
| 1,653,572 | A | | 12/1927 | Jackson |
| 1,926,027 | A | | 9/1933 | Biggs |

(Continued)

FOREIGN PATENT DOCUMENTS

AU            91/77110 B       11/1991

(Continued)

OTHER PUBLICATIONS

Mask 1 Photographs, Respironics Inc.. Reusable Full Mask (small) Part #452033 Lot #951108.

(Continued)

*Primary Examiner*—Kevin C Sirmons
*Assistant Examiner*—Clinton Ostrup
(74) *Attorney, Agent, or Firm*—Nixon & Vanderhye P.C.

(57) ABSTRACT

An adjustable forehead support for a nasal mask. The present invention discloses an adjustable forehead support for a nasal or full-face mask wherein the forehead support may be adjusted for the different shapes and sizes of a facial profile. The forehead support utilizes a dual-arm system which adjusts the position of the forehead support vis-à-vis the mask and/or air flow tube. The angle of the mask to the face may be adjusted with the present invention.

45 Claims, 5 Drawing Sheets

U.S. PATENT DOCUMENTS

| | | | |
|---|---|---|---|
| 2,123,353 A | 7/1938 | Catt | |
| 2,245,969 A | 6/1941 | Francisco et al. | |
| 2,248,477 A | 7/1941 | Lombard | |
| 2,254,854 A | 9/1941 | O'Connell | |
| 2,287,353 A * | 6/1942 | Minnick | 128/100.1 |
| 2,317,608 A | 4/1943 | Heidbrink | |
| 2,371,965 A | 3/1945 | Lehmberg | |
| 2,376,671 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,590,006 A | 3/1952 | Gordon | |
| 2,617,751 A * | 11/1952 | Bickett | 428/166 |
| 2,664,084 A * | 12/1953 | Hammermann | 128/203.25 |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,182,659 A | 5/1965 | Blount et al. | |
| 3,189,027 A | 6/1965 | Bartlett | |
| 3,193,624 A | 7/1965 | Webb et al. | |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,750,333 A | 8/1973 | Vance | |
| 3,752,157 A | 8/1973 | Malmin | |
| 3,796,216 A | 3/1974 | Schwarz | |
| 3,799,164 A | 3/1974 | Rollins | |
| D231,803 S | 6/1974 | Huddy | |
| 3,830,230 A | 8/1974 | Chester | |
| 4,077,404 A | 3/1978 | Elam | |
| D250,131 S | 10/1978 | Lewis et al. | |
| 4,167,185 A | 9/1979 | Lewis | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,328,797 A | 5/1982 | Rollins, III et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,467,799 A | 8/1984 | Steinberg | |
| 4,522,639 A | 6/1985 | Ansite et al. | |
| 4,558,710 A | 12/1985 | Eichler | |
| 4,616,647 A | 10/1986 | McCreadie | |
| 4,622,964 A | 11/1986 | Flynn | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| D293,613 S | 1/1988 | Wingler | |
| 4,732,147 A * | 3/1988 | Fuller | 128/207.18 |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,938,210 A | 7/1990 | Shene | |
| 4,938,212 A | 7/1990 | Snook et al. | |
| 4,944,310 A | 7/1990 | Sullivan | |
| D310,431 S | 9/1990 | Bellm | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,069,205 A | 12/1991 | Urso | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,980 A | 8/1992 | Haughey et al. | |
| 5,140,982 A | 8/1992 | Bauman | |
| 5,159,938 A | 11/1992 | Laughlin | |
| 5,178,138 A | 1/1993 | Walstrom et al. | |
| D334,633 S | 4/1993 | Rudolph | |
| 5,220,699 A | 6/1993 | Farris | |
| 5,231,983 A | 8/1993 | Matson et al. | |
| 5,233,978 A | 8/1993 | Callaway | |
| 5,243,971 A | 9/1993 | Sullivan et al. | |
| 5,265,595 A | 11/1993 | Rudolph | |
| 5,279,289 A | 1/1994 | Kirk | |
| 5,280,784 A | 1/1994 | Kohler | |
| 5,311,862 A | 5/1994 | Blasdell et al. | |
| 5,322,057 A | 6/1994 | Raabe et al. | |
| 5,322,059 A | 6/1994 | Walther | |
| 5,343,878 A | 9/1994 | Scarberry et al. | |
| 5,357,951 A | 10/1994 | Ratner | |
| 5,372,130 A | 12/1994 | Stern et al. | |
| 5,388,273 A * | 2/1995 | Sydor et al. | 2/255 |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,481,763 A | 1/1996 | Brostrom et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A * | 8/1996 | Lomas | 2/173 |
| 5,546,936 A | 8/1996 | Virag et al. | |
| 5,558,090 A | 9/1996 | James | |
| RE35,339 E | 10/1996 | Rapoport | |
| 5,560,354 A | 10/1996 | Berthon-Jones et al. | |
| 5,570,682 A | 11/1996 | Johnson | |
| 5,570,689 A | 11/1996 | Starr et al. | |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |

| | | | |
|---|---|---|---|
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,814 A | 2/1998 | Ebers | |
| 5,724,965 A | 3/1998 | Handke et al. | |
| 5,746,201 A | 5/1998 | Kidd | |
| 5,813,423 A | 9/1998 | Kirchgeorg | |
| 5,832,918 A | 11/1998 | Pantino | |
| 5,921,239 A | 7/1999 | McCall et al. | |
| 5,937,851 A | 8/1999 | Serowski et al. | |
| 6,044,844 A | 4/2000 | Kwok et al. | |
| 6,098,205 A | 8/2000 | Schwartz et al. | |
| 6,112,746 A | 9/2000 | Kwok et al. | |
| 6,119,693 A | 9/2000 | Kwok et al. | |
| 6,123,071 A | 9/2000 | Berthon-Jones et al. | |
| 6,152,137 A | 11/2000 | Schwartz et al. | |
| D439,326 S | 3/2001 | Hecker et al. | |
| D443,355 S | 6/2001 | Gunaratnam et al. | |
| 6,257,237 B1 | 7/2001 | Suzuki | |
| 6,341,606 B1 | 1/2002 | Bordewick et al. | |
| 6,374,826 B1 | 4/2002 | Gunaratnam et al. | |
| 6,397,847 B1 | 6/2002 | Scarberry et al. | |
| 6,463,931 B1 | 10/2002 | Kwok et al. | |
| D468,823 S | 1/2003 | Smart | |
| 6,520,182 B1 | 2/2003 | Gunaratnam | |
| 6,532,961 B1 | 3/2003 | Kwok et al. | |
| 6,557,556 B2 | 5/2003 | Kwok | |
| D484,237 S | 12/2003 | Lang et al. | |
| 6,679,261 B2 | 1/2004 | Lithgow et al. | |
| 6,691,707 B1 | 2/2004 | Gunaratnam et al. | |
| 6,691,708 B2 | 2/2004 | Kwok et al. | |
| D492,992 S | 7/2004 | Guney et al. | |
| 6,918,390 B2 | 7/2005 | Lithgow et al. | |
| 2003/0084904 A1 | 5/2003 | Gunaratnam | |
| 2003/0221691 A1 | 12/2003 | Biener et al. | |
| 2004/0045550 A1 | 3/2004 | Lang et al. | |
| 2004/0060561 A1 | 4/2004 | Kwok et al. | |
| 2005/0155605 A1 | 7/2005 | Lithgow et al. | |

FOREIGN PATENT DOCUMENTS

| | | | |
|---|---|---|---|
| AU | 94/64816 B | 12/1994 | |
| AU | 95/16178 B | 7/1995 | |
| AU | 9459430 | 2/1996 | |
| AU | A 32914/95 | 2/1996 | |
| AU | A 41018/97 | 4/1998 | |
| AU | A 89312/98 | 1/1999 | |
| CA | 1039144 | 9/1928 | |
| DE | 459 104 | 4/1928 | |
| DE | 701 690 | 1/1941 | |
| DE | 159396 | 6/1981 | |
| DE | 3015279 A1 | 10/1981 | |
| DE | 3345067 A1 | 6/1984 | |
| DE | 3537507 | 4/1987 | |
| DE | 3539073 A1 | 5/1987 | |
| DE | 4004157 C1 | 4/1991 | |
| DE | 4343205 A1 | 6/1995 | |
| DE | 197 35 359 | 1/1998 | |
| DE | 297 23 101 | 7/1998 | |
| DE | 298 10846 U1 | 8/1998 | |
| EP | 0 054 154 | 10/1981 | |
| EP | 0 252 052 A1 | 1/1988 | |
| EP | 0 264 772 A1 | 4/1988 | |
| EP | 0 386 605 A1 | 2/1990 | |
| EP | 0427474 A2 | 5/1991 | |
| EP | 0 462 701 A1 | 12/1991 | |
| EP | 0 602 424 | 11/1993 | |
| EP | 0 608 684 A1 | 8/1994 | |
| EP | 0 0697 225 | 7/1995 | |
| EP | 178 925 A2 | 4/1996 | |
| EP | 0 747 078 A2 | 12/1996 | |
| EP | 0 821 978 | 2/1998 | |
| FR | 2 574 657 A1 | 6/1986 | |
| FR | 2 658 725 A1 | 8/1991 | |
| FR | 2 749 176 | 12/1997 | |
| GB | 1395391 | 5/1975 | |
| GB | 1 467 828 | 3/1977 | |
| GB | 2145335 A | 3/1985 | |
| GB | 2147506 A | 5/1985 | |
| GB | 2 164 569 A | 3/1986 | |
| GB | 2 267 648 A | 12/1993 | |
| JP | 09/216240 A | 8/1997 | |
| WO | WO 80/01044 | 5/1980 | |
| WO | WO 82/03548 | 10/1982 | |
| WO | WO 86/06969 | 12/1986 | |
| WO | WO 87/01950 | 4/1987 | |
| WO | WO 91/03277 | 3/1991 | |
| WO | WO 92/15353 | 9/1992 | |
| WO | WO 92/20395 | 11/1992 | |
| WO | WO 93/01854 | 2/1993 | |
| WO | WO 94/02190 | 2/1994 | |
| WO | WO 94/16759 | 8/1994 | |
| WO | WO 94/20051 | 9/1994 | |
| WO | WO 95/02428 | 1/1995 | |
| WO | WO 96/17643 | 6/1996 | |
| WO | WO 96/25983 | 8/1996 | |
| WO | WO 96/39206 | 12/1996 | |
| WO | WO 97/07847 | 3/1997 | |
| WO | WO 97/41911 | 11/1997 | |
| WO | WO 98/04310 | 2/1998 | |
| WO | WO 98/11930 | 3/1998 | |
| WO | WO 98/18514 | 5/1998 | |
| WO | WO 98/24499 | 6/1998 | |
| WO | WO 98/26829 | 6/1998 | |
| WO | WO 98/26830 | 6/1998 | |
| WO | WO 98/48878 | 11/1998 | |

OTHER PUBLICATIONS

Mask 2 Photographs, Puritan—Bennett, Adam Curcuit, Shell Part #231700, Swivel Part #616329-00, Pillows (medium) Part #616324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port. Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc.. Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc.. Soft Cap (medium), Part #302142.
Mask 11 Photographs, Weinmann: Hamburg, Nasalmaskensystem mit Schalldämpfer (medium), Part #WN23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photographs, Hans Rudolph Inc.. Hans Rudolph Silicone Rubber Face Mask/8900.
Photograph of Weinmann Mask, acquired prior to 1998.
Sullivan Mirage brochure, © 1997, ResMed Limited.

Sullivan Mirage brochure, © 1998, ResMed Limited.

Somotron CPAP-Gerat WM 2300 Instruction Manual, Weinmann Hamburg, 11 pages, 1991.

9 photographs of Weinmann mask, WM 23122, 1991.

The ResMed Range of Mask Systems, product brochure, Nov. 1995, 4 pages.

U.S. Appl. No. 60/227,472, filed Aug. 2000, Lithgow et al.

* cited by examiner

FOREHEAD SUPPORT FOR FACIAL MASK

CROSS REFERENCE TO RELATED APPLICATIONS

This application is a continuation of U.S. application Ser. No. 10/661,570, filed Sep. 15, 2003, now U.S. Pat. No. 6,997, 188, which is a continuation of U.S. application Ser. No. 10/230,169, filed Aug. 29, 2002, now U.S. Pat. No. 6,691, 708, which is a divisional of U.S. application Ser. No. 09/608, 440, filed Jun. 30, 2000, now U.S. Pat. No. 6,463,931, which is a continuation of U.S. application Ser. No. 09/008,708, filed Jan. 16, 1998, now U.S. Pat. No. 6,119,693, each incorporated herein by reference in its entirety.

FIELD OF THE INVENTION

The present invention Generally relates to an improved comfort device to be used with a nasal mask. In particular, the device is useful in combination with masks which are used for the treatment of respiratory conditions and assisted respiration. The invention assists in fitting the mask to the face as well.

BACKGROUND OF THE INVENTION

Nasal masks are commonly used in the treatment of respiratory conditions and sleep disorders by delivering a flow of breathable gas to a patient to either assist the patient in respiration or to provide a therapeutic form of gas to the patient to prevent sleep disorders such as obstructive sleep apnea. These nasal masks typically receive a gas through a supply line which delivers gas into a chamber formed by walls of the mask. The mask is generally a semi-rigid mask which has a face portion which encompasses at least the wearer's nostrils. Additionally, the mask may be a full face mask. The mask is normally secured to the wearer's head by straps. The straps are adjusted to pull the mask against the face with sufficient force to achieve a gas tight seal between the mask and the wearer's face. Gas is thus delivered to the mask through the aperture to the wearer's nasal passages and/or mouth.

One of the problems that arises with the use of the mask is that in order for the straps to be tight, the mask is compressed against the wearer's face and may push unduly hard on the wearer's nose. Additionally, the mask may move around vis-à-vis the wearer's face. Thus, there has been provided a forehead support, which provides a support mechanism between the mask and the forehead. This forehead support prevents both the mask from pushing too strongly against the wearer's nose and/or facial region as well as minimize movement of the mask with the addition of a contact point between the mask and the wearer's head as well as minimize uncomfortable pressure points of the mask. Additionally, the forehead support may prevent the air flow tube from contacting the wearer's forehead or face.

Prior to the present invention, the forehead supports were generally a single cushion with a single contact point which may be adjustable by rotation of a screw, with the single cushion pushing on the forehead at a single point. This is oftentimes uncomfortable for the patient, and the adjustability of the distance of the pad for different forehead protuberances oftentimes was difficult if not impossible to be performed. Additionally, a single contact point does not provide necessary lateral support to the mask. Finally, a single contact point may apply too much pressure at the single point.

Examples of prior art nasal masks are shown in U.S. Pat. Nos. 4,782,832 and 5,243,971.

There is a need for an improved forehead support for nasal and facial masks which adjusts to different angles on the face.

There is a need for a forehead support for nasal masks which may be adjusted to different forehead shapes.

There is a need for a multi-point forehead support for nasal masks.

These and other advantages will be described in more detail below.

SUMMARY OF THE INVENTION

The present invention is directed to an improved forehead support for nasal and facial masks. In particular, the present invention utilizes a dual cantilevered forehead-support which preferably utilizes dual contacts which are arranged at an obtuse angle with respect to one another and which may be easily adjusted for different forehead protuberances. Preferably, the forehead support has two arms extending from the mask or gas supply line, with the two arms engagable into a bridge system wherein the arms may be adjusted to different positions on the bridge allowing optimal positioning of the mask on the face. This achieves even pressure of the mask on the face. The mask also provides an excellent fit which limits movement of the mask during sleep. The forehead support is adjustable such that the support is closer or further away from the front plane of the facial mask. The bridge supports the pad or pads which contact the wearer's forehead. The support also may allow the mask to be secured such that more pressure is applied to one area of the mask, to seal a leak for example.

The present invention allows the mask user to adjust the angle of the mask to the face. This is possible due to the two point contact of the forehead support to the forehead working in combination with the point of contact of the mask to the face. The system thus has three points of contact, wherein the forehead pads provide two contact points and the mask to the face is a third point of contact. Adjusting the angle of the forehead pads or the distance of the legs to the forehead pads adjusts the angle of the mask vis-à-vis the face of the user. This unique system provides a mask system which can be adjusted to fit the different face angles or profiles required by users.

DETAILED DESCRIPTION OF THE PREFERRED EMBODIMENT

Figure 1:
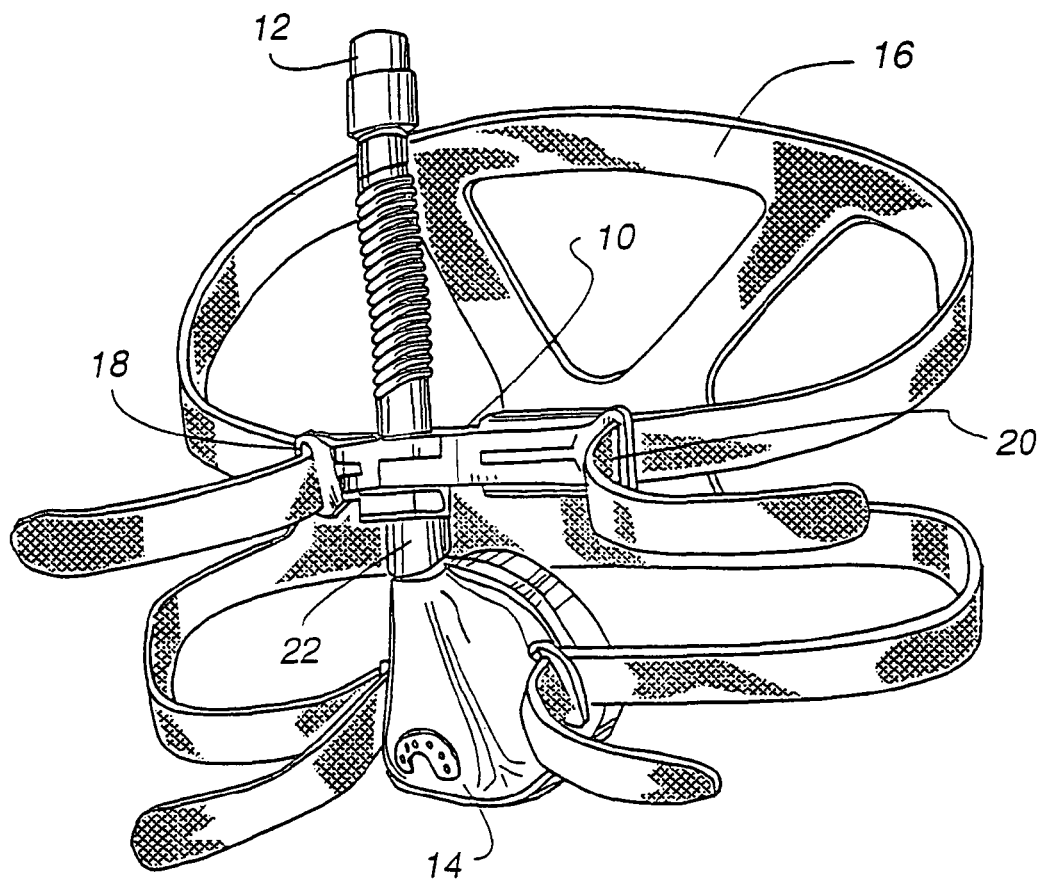
FIG. 1 is a perspective view of the forehead support of the present invention attached to a mask, headgear and a as supply tube.

FIG. 1 shows a general perspective view of the forehead support 10 of the present invention. The forehead rest or support 10 is attached to an extending airflow tube 12 from the mask 14. The mask 14 and forehead support 10 are shown with headgear 16 which secures the mask 14 to the head of a patient. The headgear 16 may take a variety of forms, with one example being shown as 16. As can be seen in FIG. 1, preferably the headgear 16 loops through the forehead support 10 at 18 and 20. This pulls the forehead support 10 against the forehead, thus creating a snugly fitted mask 14 and also provides a stabilizing member for the mask 14.

The mask 14, shown in FIG. 1 is merely one example of a mask which can be used with a forehead support, but any respiratory mask could be used. A full face mask which may cover the entire face or just both the nose and mouth could be used, for example. Additionally, the airflow tube 12 could be extending from the bottom of the mask 14, thus the tube 12 supporting the forehead support 10 would terminate above forehead support 10. If the airflow tube 12 extended in a downward or other direction from the mask 14, then preferably a post would extend up from the mask 14 (this post position is referenced as 22). This post 22 would terminate slightly above where forehead support 10 is shown secured to tube 12. Thus the forehead support 10 would be secured to the post in this alternative embodiment.

Figure 2:
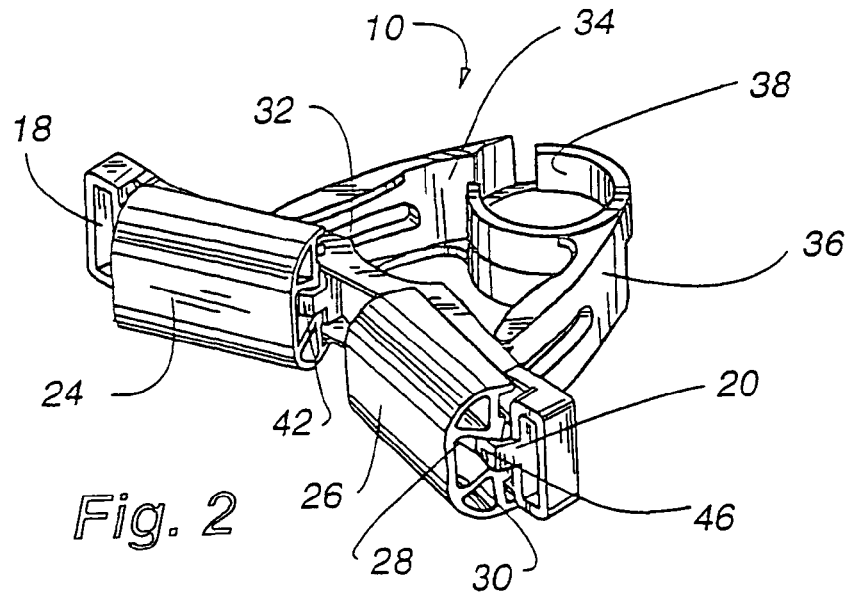
FIG. 2 is a perspective view of the forehead support of the present invention removed from the mask and gas line.

FIG. 2 discloses the preferred construction of the forehead support 10 of the present invention. The forehead support 10 has pads 24 and 26. These pads 24 and 26 are the actual contact points of the forehead support 10 to the forehead. Pads 24 and 26 are preferably made of a deformable elastomeric material which retains its original shape upon release of pressure and provides the wearer with increased comfort and stability. As can be seen in the preferred embodiment, the forehead pads 24 and 26 have an annular interior construction with two retaining walls 28 and 30. The retaining walls 23 and 30 provide structural integrity to the forehead contact support pads yet allow the pads to be deformed. The deformation preferably occurs by deflection of the pad walls. The pads also may be solid pads. The support pads 24 and 26 are mounted to the bridge 32. The bridge 32 provides basically three purposes to the forehead support 10. First off, it acts as a securing means for forehead pads or cushions 24 and 26. Second of all, it has annular spaces 18 and 20 which receive the optional headgear 16 shown in FIG. 1. Finally, it receives arms 34 and 36, which may be adjusted, as described below. The bridge 32 and arms 34 and 36 operate in a cantilever fashion and are preferably made of a polymeric material, which may be easily molded, preferably injection molded. Arms 34 and 36 are secured to bridge 32 by an adjustable locking mechanism which is better illustrated in the figures below. Additionally, arms 34 and 36 join together to create an annular space 38 which may receive airflow tube 12 which is preferably connected to a flow generator to generate breathable air or some type of therapeutic gas. Arms 34 and 36 preferably create an operational hinge. The tube 12 may be an axis of this hinge. The hinge could also be a flexible membrane and not a rotational or axial hinge. Alternatively, the tube may extend through annular space 38 and terminate as described above (in the "post" embodiment) if the air flow tube is connected to another port on the mask.

Figures 3, 4:
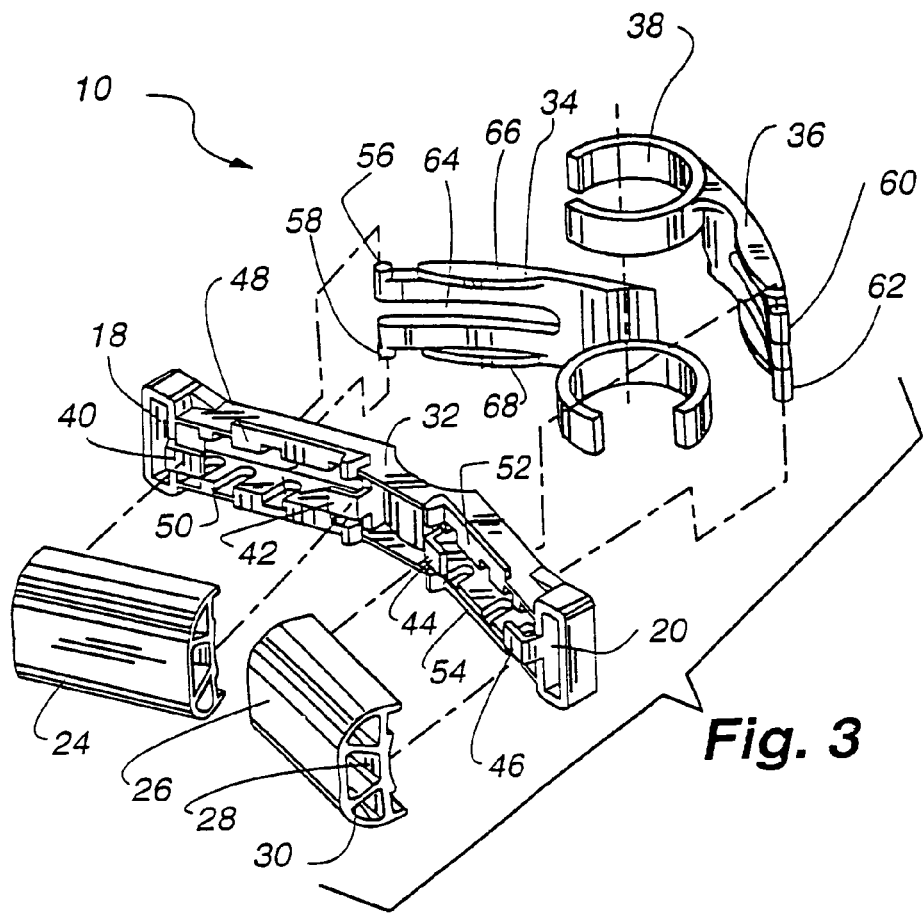
FIG. 3 is an exploded view of the forehead support of the present invention.
FIG. 4 is a side view of the present invention secured to a mask.

FIG. 3 is an exploded view of FIG. 2 and shows the forehead support 10 in greater detail. FIG. 3 discloses how bridge 32 is configured such that forehead pads 24 and 26 may be secured thereto. In particular, tongues 40, 42, 44 and 46 all engage forehead pads 24 and 26 by entering the interior space of the pads. This is shown in FIG. 2 wherein tongues 42 and 46 are shown securing pads 24 and 26 respectively by entering the annular space of the pads 24 and 26. Additionally, there may be engaging surfaces such as 48, 50, 52 and 54, as shown in FIG. 3, which engage an inner side wall of forehead pads 24 and 26. The means by which the forehead pads are secured to the bridge 32 can be done in many manners, and one skilled in the art can come up with numerous methods of achieving this securement. Two sided tape may be used, protruding pegs and apertures on the forehead pad may be used or many other methods. What is desirable is that the forehead pad(s) may be replaced after extended use or, in a clinical setting, with each new patient. The method of securement of the pad(s) to the support is not a limiting feature of the present invention.

The type of forehead pad may also vary, it may include a solid foam sponge, a stuffed pad, a dual durometer foam which may be a single pad or multiple pads attached together, or many other known pads which would impart comfort when placed directly on the forehead. Finally, a single pad which extends all the way across bridge 32 may be used or more than two pads may be used.

Bridge engaging pins 56, 58, 60 and 62 are shown in FIG. 3. As will be more apparent in the figures below, these engaging pins provide for the adjustability of the forehead support 10 of the present invention. There are pin receiving means located on the bridge 32 which receive pins 56, 58, 60 and 62. The pins 56, 58, 60 and 62 are merely one example of how the arms 34 and 36 may be secured to bridge 32. There are other designs which would work just as well as the pin designs. Such designs are known to those skilled in the art. Additionally, there is a space or recess at arms 34 and 36 shown clearly on arm 34 as 64. The purpose of this space 64 is so that the user may compress arm 34 and thus press 56 and 58 together by pressing on surfaces 66 and 68. The purpose of the compression is such that the distance between prongs 56 and 58 is decreased and thereby they may be inserted and locked into bridge 32. The structure and method of this insertion will be described in further detail below.

FIG. 4 is a side view of the mask 14 and forehead support 10 of the present invention. The mask is shown as 14 with a dotted line showing the nose of a wearer 70 and the dotted line showing the forehead 72 of the wearer. Pad 26 is shown compressed by the forehead of the individual wearing the mask.

Figure 5:
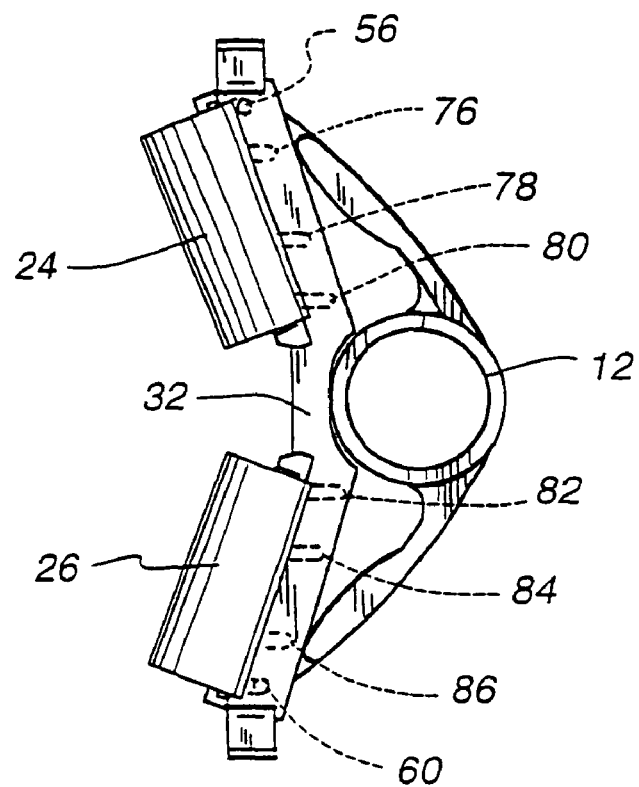
FIG. 5 is a top view of the forehead support of the present invention in a first position.

FIG. 5 is a top view of the forehead support 10 of the present invention taken along lines 5 of FIG. 4. Also, the mask 14 is not shown in FIG. 5. This figure illustrates the forehead support 10 in a position wherein the forehead support is the closest to the tube 12 (shown as merely a space in FIGS. 5-8). The bridge 32 is shown essentially in contact with tube 12. The pins 56, 58, 60 and 62 are shown in their furthest position from the center of the bridge 32. This position may be utilized by someone with a large, protruding or bulbous forehead, or a high nasal bridge, or someone who prefers the airflow tube to be snug against their forehead.

Figure 6:
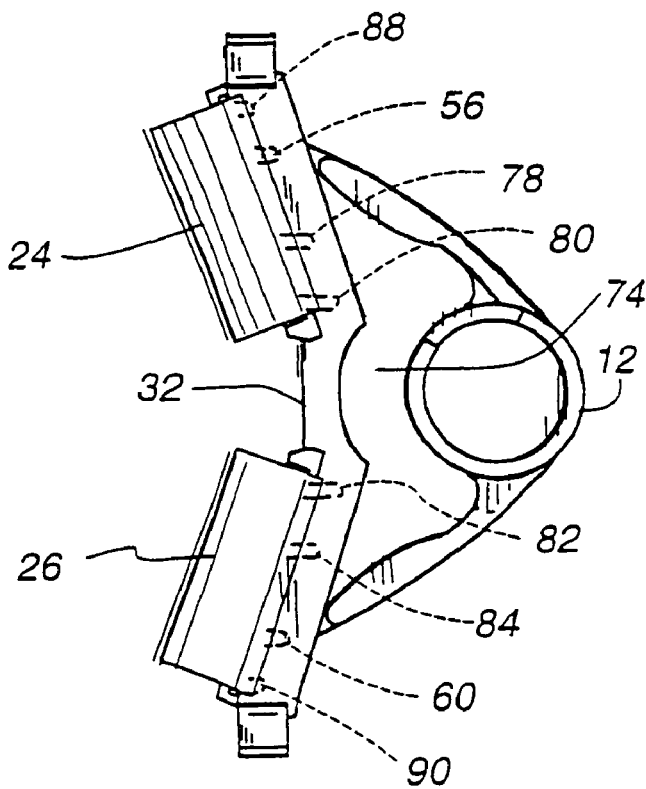
FIG. 6 is a top view of the forehead support of the present invention in a second position.

FIG. 6 shows the same forehead support in the next position, wherein the bridge 32 is moved away from tube 12 such that there is a gap 74 between bridge 32 and tube 12. As is visible from the figure, the forehead support 10 is now moved further away from tube 12, and is positioned differently than in FIG. 5. This may be configured to fit someone with a less protruding forehead, or someone who wants the flexible tube further from their head than is possible in FIG. 5.

Figure 7:
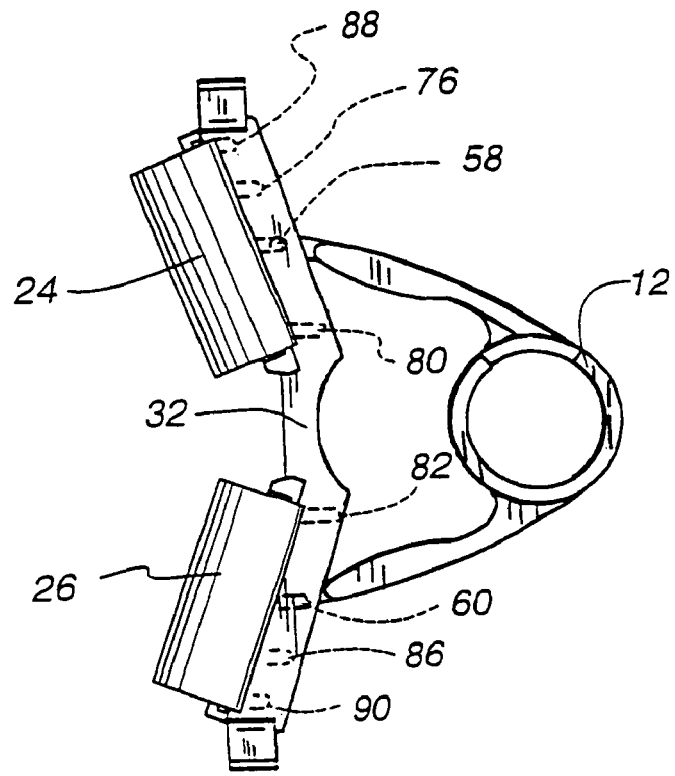
FIG. 7 is a top view of the forehead support of the present invention in a third position.
Figure 8:
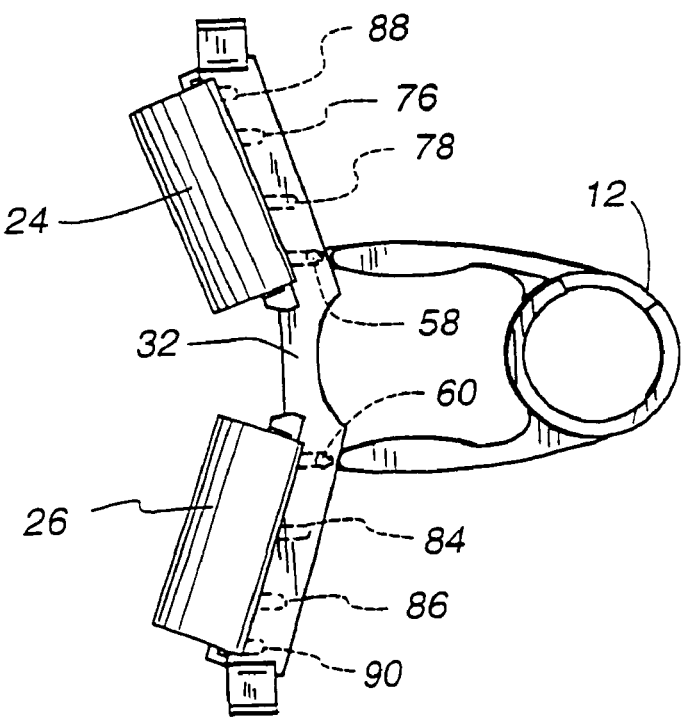
FIG. 8 is a top view of the forehead support of the present invention in a fourth position.

FIGS. 7 and 8 show the third and fourth position for the forehead support of the present invention. Although the present embodiment shows a four-positioned forehead support, the number of slots, shown as 76, 78, 80, 82, 84 86, 88 and 90 may be varied. There may be more or fewer slots, or there may just be one single slot wherein pins 56 and 58 slides transversely across bridge 32 and has locking recesses located along the slide. Additionally, the adjustments do not have to be uniform. In other words, the right side may be adjusted to slot 88 where the left side may be adjusted to slot 84 for some particular patient. There may also be more slots or adjustments on one side of the bridge as compared to the other side of the bridge. Finally, the arms may be coupled such that movement of just one arm moves the other arm in a likewise manner.

Figure 9:
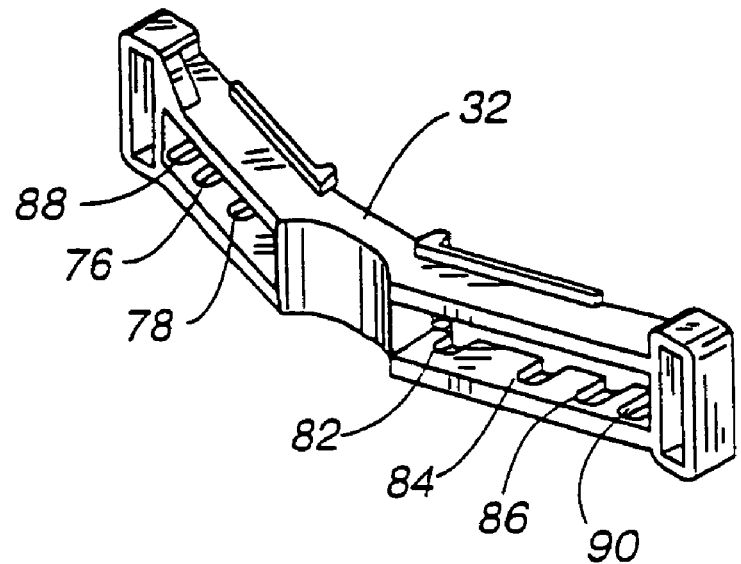
FIG. 9 is a front view of the bridge of the present invention.

FIG. 9 shows an isolated view of bridge 32. The slots 76, 78, 82, 84, 86, 88 and 90 are visible from this view. The slots are configured such that prongs 56, 58, 60 and 62 may be inserted therein. There is a mirror set of slots on the upper portion of bridge 32 which are not visible in FIG. 9. Again, there can be additional slots, fewer slots, or different methods of locking the arms 34 and 36 to various positions along the bridge 32. What is important to the present invention is that the bridge 32 with the accompanying pads 24 and 26 may be positioned to a variety of distances between the tube 12 and the pads 24 and 26. Additionally, the pad may be one continuous pad, three pads, five pads, four pads, etc. There also may a double bridge used, wherein there could be a total of two or more pads with two bridges.

Figure 10:
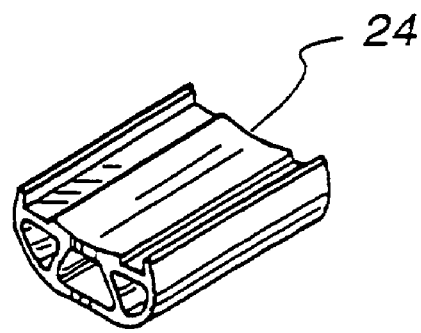
FIG. 10 is a single pad of the present invention.

FIG. 10 is a perspective view of the preferred forehead pad of the present invention. As indicated above, there could be many shapes or variations of a forehead pad and type of forehead pad or the shape of forehead pad is not limited in the present invention.

It is to be understood that while the invention has been described above in conjunction with preferred specific embodiments, the description and examples are intended to illustrate and not limit the scope of the invention, which is defined by the scope of the appended claims.

We claim:

1. A mask assembly for delivering a flow of pressurized breathable gas to a patient, comprising:
    a face contact portion configured to engage the patient's face and encompass at least the patient's nostrils;
    a forehead support connected to the face contacting portion;
    a pad formed of deformable material, comprising
        an outer wall having a first side configured to engage a user's forehead and a second side having engaged surfaces configured to rest against engaging surfaces of the forehead support;
        at least one retaining wall provided between the first side and the second side; and
        at least one retained portion configured to be retained by a retainer formed on the forehead support, wherein a space is defined between the outer wall and the engaged surfaces, the space comprises a substantially constant cross sectional profile, and the outer wall, the at least one retaining wall, and the engaged surfaces are formed of a deformable elastomeric material, wherein deformation of the pad occurs by deflection of at least the outer wall and the at least one retaining wall; and
    a headgear configured to maintain the face contact portion in contact with the patient's face and the pad in contact with the patient's forehead.

2. A mask assembly according to claim 1, wherein the forehead support comprises a slot, the slot comprises the engaging surfaces on opposite sides of the slot, and an inner wall of the pad is in contact with the engaging surfaces.

3. A mask assembly according to claim 2, wherein the slot has a length generally equal to a length of the pad.

4. A mask assembly according to claim 3, further comprising a retainer at an end of the slot configured to engage an end of the pad and retain the inner wall in contact with the engaging surfaces.

5. A mask assembly according to claim 4, wherein the forehead support comprises an annular space to receive a first strap of the headgear connected to the forehead support.

6. A mask assembly according to claim 5, wherein the annular space is adjacent the slot.

7. A mask assembly according to claim 6, wherein headgear comprises a second strap configured to maintain the face contact portion in contact with the patient's face.

8. A mask assembly according to claim 7, wherein the first and second straps are connected by third and fourth straps.

9. A mask assembly according to claim 1, further comprising at least one vent in the face contact portion.

10. A mask assembly according to claim 1, wherein the face contact portion comprises a mask shell coupled to a facial cushion support structure including a cheek region and a nasal bridge region.

11. A mask assembly according to claim 10, wherein the facial cushion support structure is configured to encompass the patient's nose and mouth.

12. A mask assembly according to claim 1, wherein the pad further comprises an inner wall being in contact with the forehead support, and the inner wall and outer wall define an annular interior of the forehead pad that is open at opposite ends of the pad.

13. A mask assembly according to claim 1, wherein the deformable material retains its shape.

14. A mask assembly according to claim 1, wherein the cross sectional profile is substantially constant along a length of the pad.

15. A mask for delivering a flow of pressurized breathable gas to a patient, comprising:
    a shell defining a chamber adapted to fit over the nose and mouth of the patient;
    a facial cushion connected to the shell and adapted to sealingly engage the patient's face;
    a forehead support connected to the shell, the forehead support comprising two annular spaces, each annular space being configured to receive an end of a first strap of a headgear attachable to the mask; and
    a forehead pad formed of deformable material, comprising
        an outer wall having a first side configured to engage a user's forehead and a second side having engaged surfaces configured to rest against engaging surfaces of the forehead support;
        at least one retaining wall provided between the first side and the second side; and
        at least one retained portion configured to be retained by a retainer formed on the forehead support, wherein a space is defined between the outer wall and the engaged surfaces, the space comprises a substantially constant cross sectional profile, and the outer wall, the at least one retaining wall, and the engaged surfaces are formed of a deformable elastomeric material, wherein deformation of the pad occurs by deflection of at least the outer wall and the at least one retaining wall.

16. A mask according to claim 15, wherein the deformable elastomeric material retains its shape.

17. A mask according to claim 15, wherein the forehead support comprises a slot, the slot comprises engaging surfaces on opposite sides of the slot, and the second side of the forehead pad is in contact with the engaging surfaces.

18. A mask according to claim 17, wherein the slot has a length generally equal to a length of the forehead pad.

19. A mask according to claim 18, further comprising a retainers at each end of the slot, each retainer configured to engage a respective end of the pad and retain the second side in contact with the engaging surfaces.

20. A mask according to claim 19, wherein each retainer extends over a portion of the slot.

21. A mask according to claim 15, further comprising at least one vent in the shell.

22. A mask according to claim 15, wherein the facial cushion comprises a full face cushion.

23. A mask according to claim 15, further comprising a headgear strap attachment structure to receive a second strap of the headgear, wherein the headgear attachment structure is connected to the shell.

24. A mask according to claim 15, wherein the outer wall defines an open-ended annular structure.

25. A mask according to claim 15, wherein the forehead pad is between the two annular spaces.

26. A mask according to claim 15, wherein the cross sectional profile is substantially constant along a length of the pad.

27. A mask according to claim 26, wherein the at least one retaining wall comprises two retaining walls that divide the space into three sub-spaces.

28. A mask according to claim 27, wherein at least two of the three sub-spaces have different cross sectional profiles.

29. A mask according to claim 27, wherein the at least one retained portion is provided in a middle sub-space of the three sub-spaces.

30. A mask for delivering a flow of pressurized breathable gas to a patient, comprising: a shell defining a chamber adapted to fit over the nose and mouth of the patient; a facial cushion connected to the shell and adapted to sealingly engage the patient's face; a forehead support connected to the shell, the forehead support comprising two annular spaces, each annular space being configured to receive an end of a first strap of a headgear attachable to the mask; and a pad for the forehead support, the pad comprising: an open-ended annular member including an outer wall structured to engage a user's forehead; an inner wall, opposite to the outer wall, structured to be attached to the forehead support; and a space defined between the inner and outer walls, wherein the outer wall and the inner wall are made of a deformable elastomeric material that retains its shape, wherein deformation of the pad occurs by deflection of at least the outer wall.

31. A mask according to claim 30, further comprising at least one retaining wall between the outer wall and the inner wall.

32. A mask according to claim 31, wherein the at least one retaining wall comprises two retaining walls that divide the space into three sub-spaces.

33. A mask according to claim 31, wherein the retaining wall is formed of the deformable elastomeric material that retains it shape.

34. A mask according to claim 30, wherein the inner wall comprises retained portions configured to be retained by retainers formed on the forehead support.

35. A mask assembly for delivering a flow of pressurized breathable gas to a patient, comprising:
a face contact portion configured to engage the patient's face and encompass at least the patient's nostrils;
a forehead support connected to the face contacting portion;
pad for the forehead support, the pad comprising:
an outer wall configured to contact a user's forehead, the outer wall having a first end and a second end;
an inner wall extending between the first end and the second end of the outer wall, the inner wall being structured to be attached to the forehead support, and the outer wall being spaced from the inner wall between the first end and the second end so as to define an open space; and
a first retaining wall and a second retaining wall extending between the inner wall and the outer wall between the first end, wherein the first and second retaining walls divide the space into first, second and third sub-spaces and the inner wall, the outer wall, the first retaining wall and the second retaining wall are formed of an elastomeric material, wherein deformation of the pad occurs by deflection of at least the outer wall and at least one of the first retaining wall and the second retaining wall; and
a headgear configured to maintain the face contact portion in contact with the patient's face and the pad in contact with the patient's forehead.

36. A mask assembly according to claim 35, wherein the forehead support comprises a slot, the slot comprises engaging surfaces on opposite sides of the slot, and the inner wall of the pad is in contact with the engaging surfaces.

37. A mask assembly according to claim 36, wherein the slot has a length generally equal to a length of the pad.

38. A mask assembly according to claim 37, further comprising a retainer at an end of the slot configured to engage an end of the pad and retain the inner wall in contact with the engaging surfaces.

39. A mask assembly according to claim 38, wherein the forehead support comprises an annular space to receive a first strap of the headgear connected to the forehead support.

40. A mask assembly according to claim 39, wherein the annular space is adjacent the slot.

41. A mask assembly according to claim 40, wherein headgear comprises a second strap configured to maintain the face contact portion in contact with the patient's face.

42. A mask assembly according to claim 41, wherein the first and second straps are connected by third and fourth straps.

43. A mask assembly according to claim 35, further comprising at least one vent in the face contact portion.

44. A mask assembly according to claim 35, wherein the face contact portion comprises a mask shell coupled to a facial cushion support structure including a cheek region and a nasal bridge region.

45. A mask assembly according to claim 44, wherein the facial cushion support structure is configured to encompass the patient's nose and mouth.

* * * * *